United States Patent [19]

Newman et al.

[11] Patent Number: 4,638,823

[45] Date of Patent: Jan. 27, 1987

[54] FLUORIDE-COATED DENTAL FLOSS

[76] Inventors: Michael G. Newman, 809 Alma Real Dr., Pacific Palisades, Calif. 90272; Fermin A. Carranza, Jr., 10577 Eastborne Ave., Los Angeles, Calif. 90024

[21] Appl. No.: 749,262

[22] Filed: Jun. 27, 1985

Related U.S. Application Data

[62] Division of Ser. No. 475,234, Mar. 14, 1983, Pat. No. 4,548,219.

[51] Int. Cl.⁴ .............................................. A61C 15/00
[52] U.S. Cl. ..................................................... 132/91
[58] Field of Search ............... 132/89, 91, 93; 424/27, 424/98, 128, 52, 70; 514/588

[56] References Cited

U.S. PATENT DOCUMENTS 3,830,246  8/1974  Gillings .................................. 132/89
4,029,113  6/1977  Guyton .................................. 132/91
4,308,880  1/1982  Grave .................................... 132/91

Primary Examiner—Gregory E. McNeill
Attorney, Agent, or Firm—Laff, Whitesel, Conte & Saret

[57] ABSTRACT

A fluoride-coated dental floss which has enhanced bactericidal activity and a process for manufacturing the product, which includes dissolving a fluoride composition in a suitable solvent, homogenizing the mixture with a melted water-soluble wax, and applying the resulting composition to dental floss.

5 Claims, No Drawings

FLUORIDE-COATED DENTAL FLOSS

This application is a division of 06/475,234 filed 03/14/83, now Pat. No. 4,548.219.

BACKGROUND OF THE INVENTION

This invention relates to fluoride-coated dental floss and, more particularly, to a process for coating dental floss with a fluoride composition and the product of that process.

One of the most successful methods for caries reduction is the application of fluoride to tooth surfaces. Once on the enamel surface, the fluoride-containing compound is effective in reducing dental caries due to remineralization of the enamel surface, fluoride substantivity, and bactericidal/static activity caused by the alteration of plaque bacterial metabolism. Of the three most readily available commercial fluorides, sodium fluoride (NaF), Acidulated Phosphate Fluoride (APF), and stannous fluoride ($SnF_2$), $SnF_2$ has been determined to be the most effective bactericidal agent. Sodium fluoride is believed to be more effective in strengthening the enamel surface of the teeth.

Another method of caries reduction for interproximal surfaces is the regular use of dental floss. Dental floss cleans the interproximal tooth surface by physical removal of plaque colonies, thus reducing the source of tooth decay.

In recent years, many investigators have attempted to combine the anticaries action of topical fluoride application and flossing by coating the dental floss itself with fluoride. Patients flossing with fluoride-impregnated floss will, in effect, be delivering the fluoride directly to the interproximal tooth surfaces and, more importantly, to subgingival areas where many periodontopathogens reside. In 1977, Chaet and Wei demonstrated that, by using an APF-impregnated dental floss, patients could increase their interproximal fluoride content three-fold over basal levels. In addition, the number of interproximal areas harboring Streptococcus mutans was reduced significantly after treatment with fluoride-impregnated dental floss. Previous in vitro studies have shown that, when floss is coated with a mixture of $SnF_2$ (1500 ppm $F^-$) in glycerin and water-soluble wax, a non-selective bactericidal effect against supragingival plaque microorganisms could be obtained. But in vitro, as well as in vivo studies, have indicated that such fluoride activity is short-lived (5–7 days).

DESCRIPTION OF THE INVENTION

We have developed a means of increasing the stability of the fluoride-floss preparation and the longevity of the fluoride activity above that obtained by previously known $SnF_2$-coated dental floss formulations. We have accomplished this result by a new process of combining fluoride with dental floss and the product of that process. This process includes dissolving a fluoride compound, e.g., stannous fluoride ($SnF_2$), in distilled water, adding the mixture to melted water-soluble wax, such as, for example, polyethylene glycol, and homogenizing the fluoride-wax composition. To facilitate solubility, the mixture of $SnF_2$ and water is heated to boiling until the $SnF_2$ is completely dissolved. The resulting liquid mixture is applied to dental floss and the fluoride-wax formulation is allowed to solidify on the floss. Where multi-filament floss is used, the fluoride-wax formulation impregnates and coats the floss.

While stannous fluoride is preferred because of its known bactericidal activity, other fluoride compounds which have been used and are known to be effective for application to tooth and gingival surfaces may be used. These compounds include NaF and APF, or combinations of fluorides, such as NaF and $SnF_2$. Depending on the fluoride compound used, other suitable solvents than those described may be used. Other water soluble waxes may be used, provided that they are non-toxic and non-irritating to the oral cavity and remain stable under the conditions to which dental floss is normally subjected during packaging, storage, and use.

EXAMPLE

Solid stannous fluoride was measured to yeild 4000 ppm $F^-$ when dissolved separately into each of three solvents: (1) glycerin, (2) melted wax, and (3) distilled water. In each case, the mixtures were heated to boiling to facilitate solubility. When the $SnF_2$ had dissolved completely in its solvent, the mixture was then added to melted water-soluble polyethylene glycol wax (a suitable water-soluble wax is sold under the trademark CARBOWAX by Challenge Products of Osage Beach, Mo.). The final mixture was used to coat sections of multi-filament unwaxed dental floss (manufactured by John O. Butler Company of Chicago, Ill.) using apparatus designed for that purpose. After allowing the $SnF_2$-wax formulation to solidify on the floss, the floss was cut into predetermined sections. The preparation of the $SnF_2$-coated waxed floss was completed under aerobic conditions.

When $SnF_2$ was added directly to the water-soluble wax, without first being dissolved in another solvent, no bactericidal activity was observed whether under aerobic or anaerobic incubation conditions. When the $SnF_2$ was dissolved in glycerin prior to its addition to the wax, a discernable bactericidal activity was present for eleven (11) days when incubated aerobically, but only six (6) days when incubated anaerobically. The best results were obtained when the $SnF_2$ was dissolved in water before addition to the wax. This floss formulation demonstrated bactericidal activity for sixty-seven (67) days when incubated either aerobically or anaerobically. When the concentration of $SnF_2$ was varied from 1000 to 6000 ppm $F^-$, the bactericidal activity did not differ appreciably over a ten-day test period.

Thus, by dissolving $SnF_2$ in water, rather than glycerin, before addition to water-soluble wax, the stability of the floss preparation can be enhanced. In vitro susceptibility studies showed that the $SnF_2$ in water formulation could maintain its bactericidal activity for sixty-seven (67) days compared to only eleven (11) days for the $SnF_2$ in glycerin formulation.

In order to extend the shelf life of the fluoride-coated floss of this invention, the finished product may be enclosed in an airtight container, such as a vacuum-sealed plastic pouch. In this way, the floss will not be exposed to the atmosphere until it is ready for use. By packaging a predetermined supply of floss in each pouch, bactericidal activity during use can be assured. One of the benefits of this invention is the ability to furnish a supply of floss (provided on a spool, for example), which, after exposure to the atmosphere can remain effective as a bactericide for more than two (2) months.

While the foregoing sets forth specific features of the invention, modifications may be made without departing from the invention. Therefore, the appended claims are to be construed to cover all equivalent structures falling within the spirit and scope of the invention.

We claim:

1. Dental floss made by dissolving a fluoride composition in water, adding the mixture to melted water-soluble wax, and applying the mixture to dental floss.

2. The article of claim 1 wherein the fluoride is present in concentrations ranging from about 1000 ppm $F^-$ to about 6000 ppm $F^-$.

3. The article of claim 1 wherein the fluoride is present in a concentration of about 4000 ppm $F^-$.

4. The article of claim 1 wherein the coated floss is sealed in an airtight container.

5. The article of claim 1 wherein the fluoride is stannous fluoride and the wax is polyethylene glycol.

* * * * *